(12) United States Patent
Sun

(10) Patent No.: US 11,642,011 B1
(45) Date of Patent: May 9, 2023

(54) PROTECTIVE COVER APPARATUS FOR AN OTOSCOPE

(71) Applicant: Yingjie Sun, Irvine, CA (US)

(72) Inventor: Yingjie Sun, Irvine, CA (US)

(*) Notice: Subject to any disclaimer, the term of this patent is extended or adjusted under 35 U.S.C. 154(b) by 317 days.

(21) Appl. No.: 16/803,311

(22) Filed: Feb. 27, 2020

(51) Int. Cl.
A61B 1/00 (2006.01)
A61B 1/04 (2006.01)
A61B 1/227 (2006.01)

(52) U.S. Cl.
CPC ...... A61B 1/00135 (2013.01); A61B 1/00101 (2013.01); A61B 1/042 (2013.01); A61B 1/227 (2013.01)

(58) Field of Classification Search
None
See application file for complete search history.

(56) References Cited

U.S. PATENT DOCUMENTS

| | | | |
|---|---|---|---|
| 4,380,998 A | 4/1983 | Kieffer, III et al. | |
| 5,919,130 A * | 7/1999 | Monroe | A61B 1/042 600/156 |
| 6,001,059 A * | 12/1999 | Elliott | A61B 1/00087 600/184 |
| 6,190,310 B1 | 2/2001 | Cook | |
| 6,383,133 B1 * | 5/2002 | Jones | A61B 1/227 600/184 |
| 7,354,399 B2 | 4/2008 | Strom et al. | |
| 8,920,313 B2 | 12/2014 | Baker et al. | |
| 2006/0252996 A1 * | 11/2006 | Goldfain | A61B 1/00188 600/200 |
| 2007/0161924 A1 | 7/2007 | Dolphin et al. | |
| 2012/0059224 A1 * | 3/2012 | Wellen | A61B 1/2275 600/200 |
| 2018/0125345 A1 * | 5/2018 | Rebella | A61B 1/00052 |

* cited by examiner

Primary Examiner — Timothy J Neal
(74) Attorney, Agent, or Firm — Plager Schack LLP; Mark H. Plager; Naomi Mann

(57) ABSTRACT

A protective cover apparatus for an otoscope to serve as a barrier between the otoscope and an ear canal of a user is provided. The otoscope includes a camera body coupled to a camera head having an attachment groove. The protective cover apparatus includes an adapter with a tubular member that attaches to the camera head of the otoscope, a sleeve coupled to the adapter and having a central tubular member and an outer flared surface protruding from the top end of the central tubular member, and a cap coupled to the top end of the tubular member of the adapter and having a central opening that permits unobstructed access to the camera head of the otoscope.

10 Claims, 4 Drawing Sheets

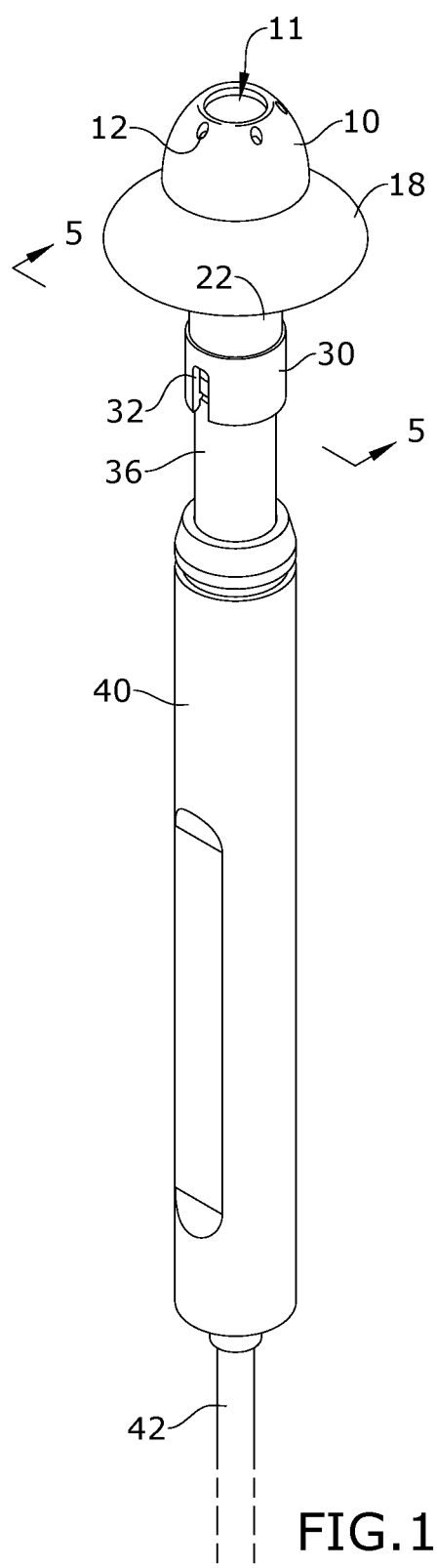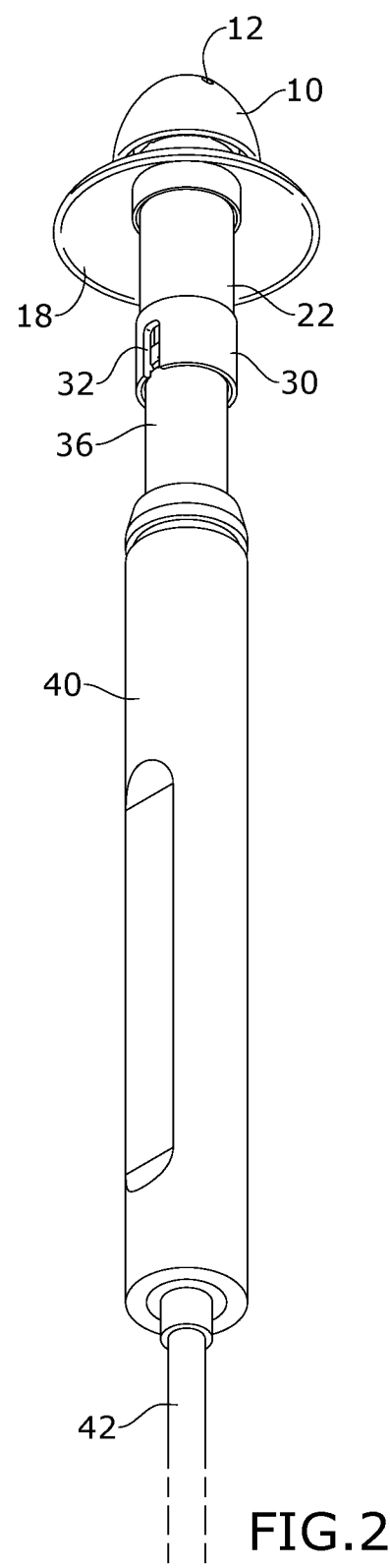

PROTECTIVE COVER APPARATUS FOR AN OTOSCOPE

BACKGROUND

The embodiments herein relate generally to otoscopes. More specifically, embodiments of the invention are directed to a protective cover apparatus for an otoscope.

Otoscopes are medical devices used by health care providers to view inside a patient's ear, including the ear canal and ear drum. Several otoscopes are digital and comprise cameras that can capture images of the inside of the patient's ear. In all these devices, the tip of the otoscope is a generally rigid and pointed member that is inserted within the patient's ear canal. This pointed tip can cause pain and/or damage to the inside of the patient's ear if it is not used and maneuvered properly therein. Further, there are health risks if the otoscope is used on multiple patients without replacing or cleaning the tip.

There exist a variety of cover tips for an otoscope as disclosed in U.S. Patent Application Publication 2007/0161924 and U.S. Pat. Nos. 8,920,313, 7,354,399, 6,190,310 and 4,380,998. These cover tips for otoscopes and/or other medical devices are undesirable because they comprise complicated components and/or do not effectively serve as a barrier between the otoscope and ear canal in a manner that is comfortable for the patient.

As such, there is a need in the industry for a protective cover apparatus for an otoscope that addresses the limitations of the prior art, which provides a simple, cost-effective, easy-to-use, comfortable and sanitary barrier between the otoscope and patient's ear. There is a further need for the protective cover apparatus to minimize the likelihood of damaging the patient's ear during use of the otoscope.

SUMMARY

In certain embodiments of the invention, a protective cover apparatus for an otoscope to serve as a barrier between the otoscope and an ear canal of a user is provided. The otoscope comprises a camera body coupled to a camera head having an attachment groove. The protective cover apparatus comprises an adapter configured to attach to the camera head of the otoscope and comprising a tubular member with a top end, a bottom end opposite the top end, an inner surface and an outer surface, a sleeve coupled to the tubular member of the adapter and comprising a central tubular member having a top end and a bottom end, the sleeve comprising an outer flared surface protruding from the top end of the central tubular member, and a cap coupled to the top end of the tubular member of the adapter and comprising a central opening that permits unobstructed access to the camera head of the otoscope, wherein the otoscope is maneuvered to permit the cap and sleeve of the protective cover apparatus to enter the ear canal of the user, thereby allowing the protective cover apparatus to serve as a barrier between the otoscope and ear canal of the user.

BRIEF DESCRIPTION OF THE FIGURES

The detailed description of some embodiments of the invention will be made below with reference to the accompanying figures, wherein the figures disclose one or more embodiments of the present invention.

FIG. 1 depicts a top perspective view of certain embodiments of the protective cover apparatus shown attached to the otoscope;

FIG. 2 depicts a bottom perspective view of certain embodiments of the protective cover apparatus shown attached to the otoscope;

DETAILED DESCRIPTION OF CERTAIN EMBODIMENTS

Figure 3:
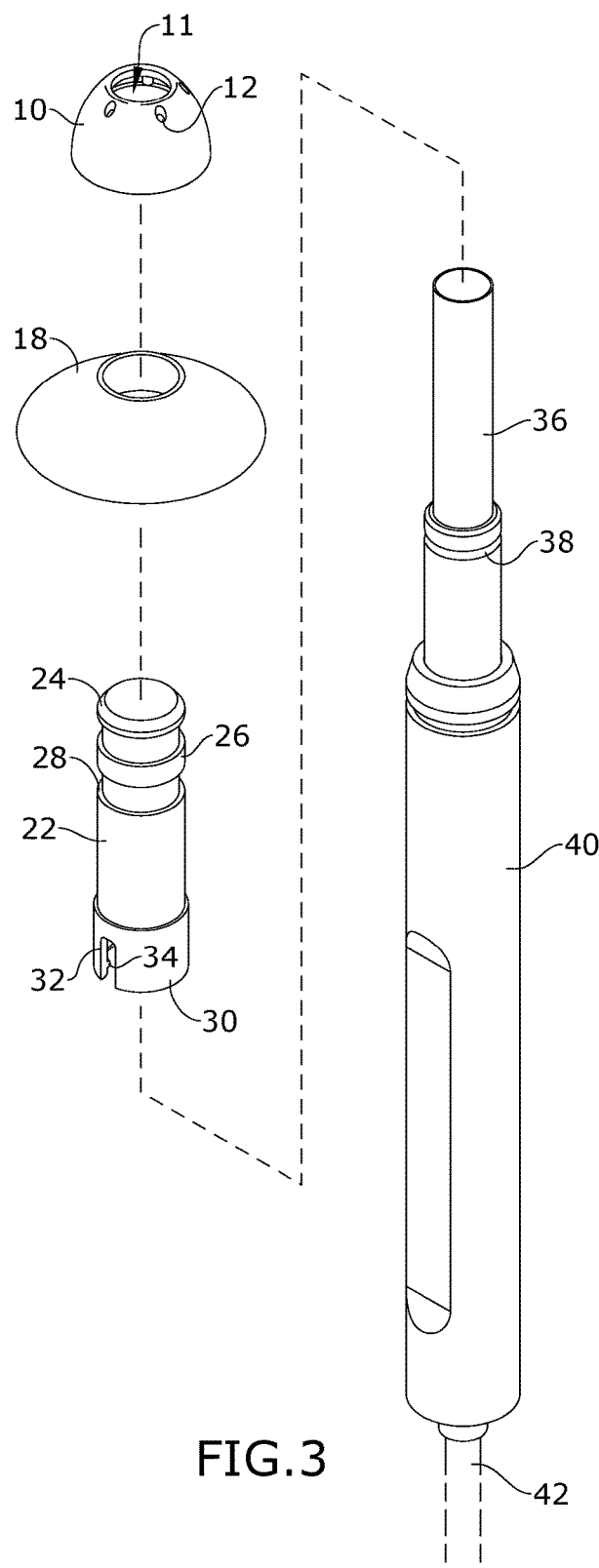
FIG. 3 depicts an exploded view of certain embodiments of the protective cover apparatus.

In certain embodiments as depicted in FIGS. 1-4, the protective cover apparatus generally comprises cap 10, sleeve 18 and adapter 22, and is configured for use with an otoscope such as a digital otoscope having camera head 36, camera body 40 and output cable 42. It shall be appreciated that the protective cover apparatus can be used with any other types of otoscopes known in the field in other embodiments.

Figures 6, 7:
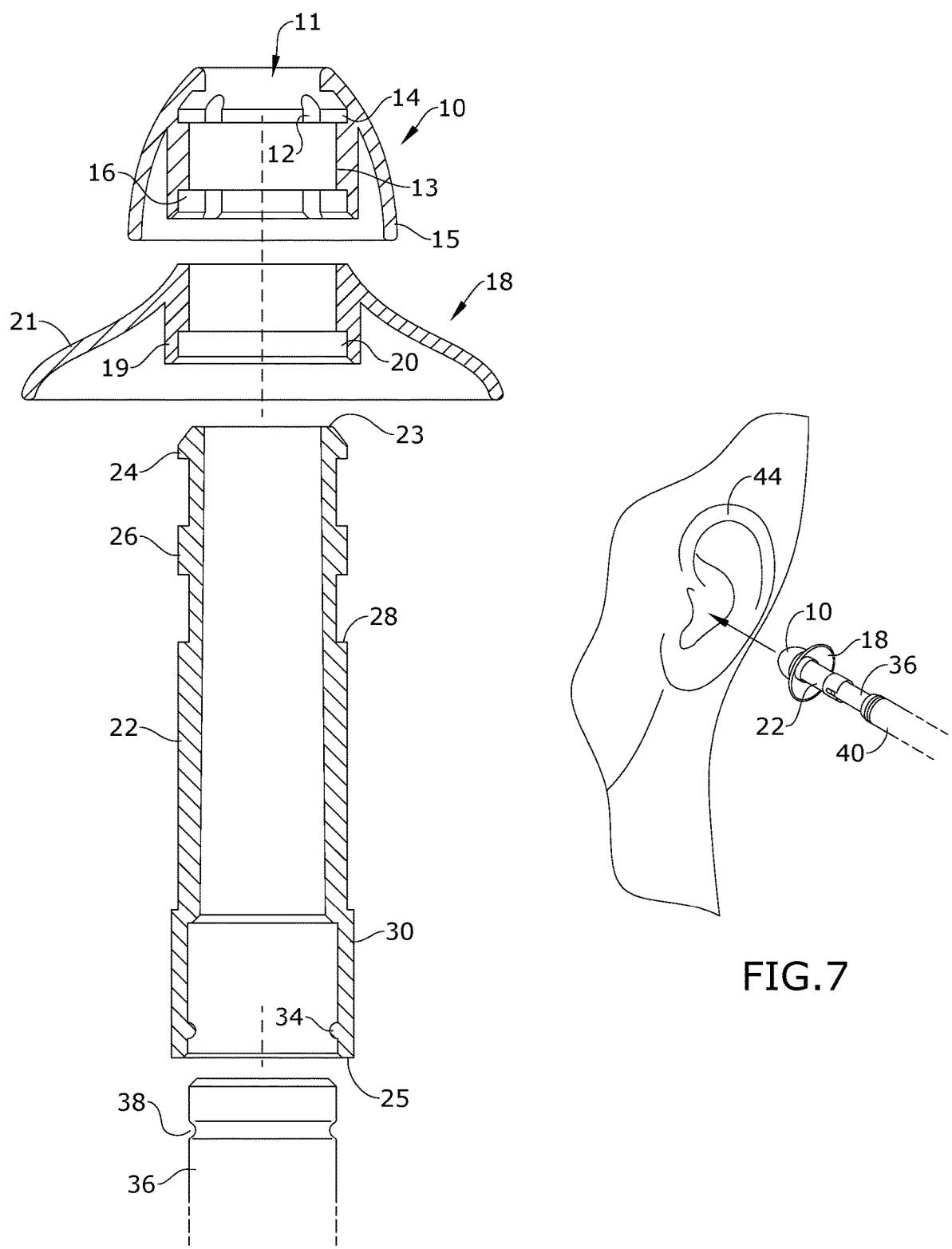
FIG. 6 depicts an exploded section view of certain embodiments of the protective cover apparatus.
FIG. 7 depicts a perspective view of certain embodiments of the protective cover apparatus shown in use.

As depicted in FIGS. 1-2 and 7, the protective cover apparatus is configured to serve as a barrier between camera head 36 of the otoscope and the ear canal of user 44. As a result, the protective cover apparatus promotes hygiene, minimizes damage to the ear canal and/or ear drum of user 44, and enhances user comfort during use of the otoscope.

Figure 4:
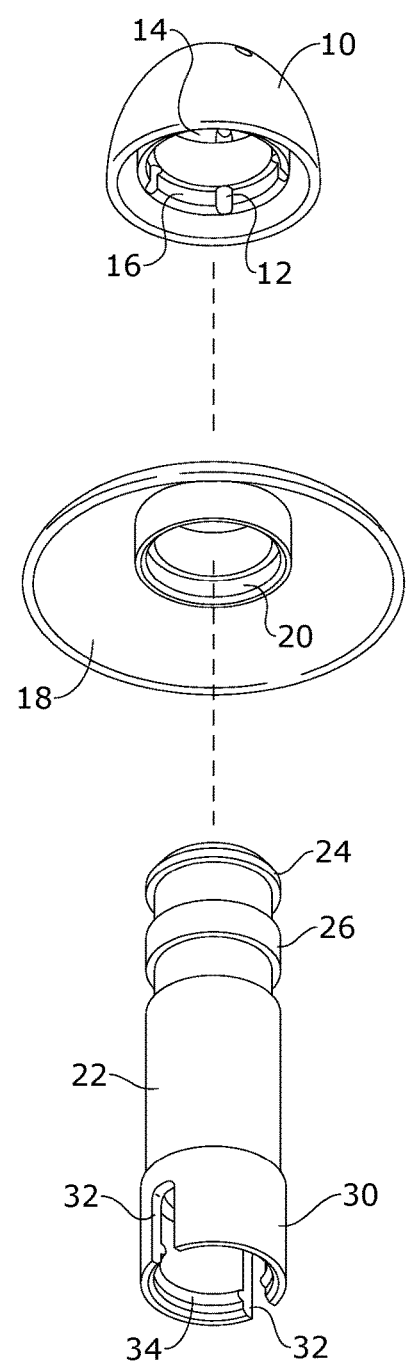
FIG. 4 depicts an exploded perspective view of certain embodiments of the protective cover apparatus.

In certain embodiments as depicted in FIGS. 3-4 and 6, adapter 22 comprises tubular member 30 with top end 23 and bottom end 25. In one embodiment, the outer surface of tubular member 30 comprises upper flange 24, lower flange 26 and ridge 28. In one embodiment, the inner surface of tubular member 30 comprises protrusion 34 proximate bottom end 25. In one embodiment as depicted in FIGS. 3-4, bottom end 25 of tubular member 30 comprises a pair of base notches 32. It shall be appreciated that any alternative number of base notches 32 can be disposed on tubular member 30 at various locations along bottom end 25 in alternative embodiments. Adapter 22 can be made from any transparent rigid or semi-rigid materials in the field including, but not limited to, polycarbonate, acrylic or other plastics.

In certain embodiments as depicted in FIGS. 1-4 and 6, sleeve 18 comprises central tubular member 19 continuously connected to outer flared surface 21. In this embodiment, outer flared surface 21 protrudes from the top end of central tubular member 19. In one embodiment, sleeve 18 is made from silicone, but can be made from any other deformable, resilient and flexible material known in the field. The dimensions of sleeve 18 can vary to accommodate different-sized ear canals of users.

Flared surface 21 is configured to insert within the ear canal of user 44. Due to the shape of flared surface 21, sleeve 18 prevents the protective cover apparatus from entering into the ear canal of user 44 to a degree that can cause discomfort and/or damage to the ear canal or other internal members of the ear. In one embodiment, central tubular member 19 of sleeve 18 comprises internal slot 20, which is configured to engage with ridge 28 of adapter 22 when sleeve 18 and adapter 22 are connected together.

In certain embodiments as depicted in FIGS. 1-4 and 6, cap 10 comprises cap central tubular member 13 continuously connected to outer cap surface 15. In this embodiment, outer cap surface 15 protrudes from the top end of cap central tubular member 13. Cap 10 comprises central opening 11, which extends longitudinally through cap central tubular member 13. In one embodiment, cap 10 is made from silicone, but can be made from any other deformable, resilient and flexible material known in the field.

The dimensions of cap 10 can vary to accommodate different-sized ear canals of users. In one embodiment as depicted in FIGS. 1, 3-4 and 6, cap 10 comprises a plurality of vents 12 disposed therethrough. Vents 12 are advantageous when the diameter of cap 10 is larger than the diameter of the ear canal of user 44. In this scenario, vents 12 allow air to flow freely through cap 10 to release any pressure therein and enhance user comfort when the protective cover apparatus is maneuvered within the ear of user 44. In an alternative embodiment, vents 12 can be removed from cap 10. Cap 10 without vents 12 is ideal when the diameter of cap 10 is smaller than the diameter of the ear canal of user 44.

Figure 5:
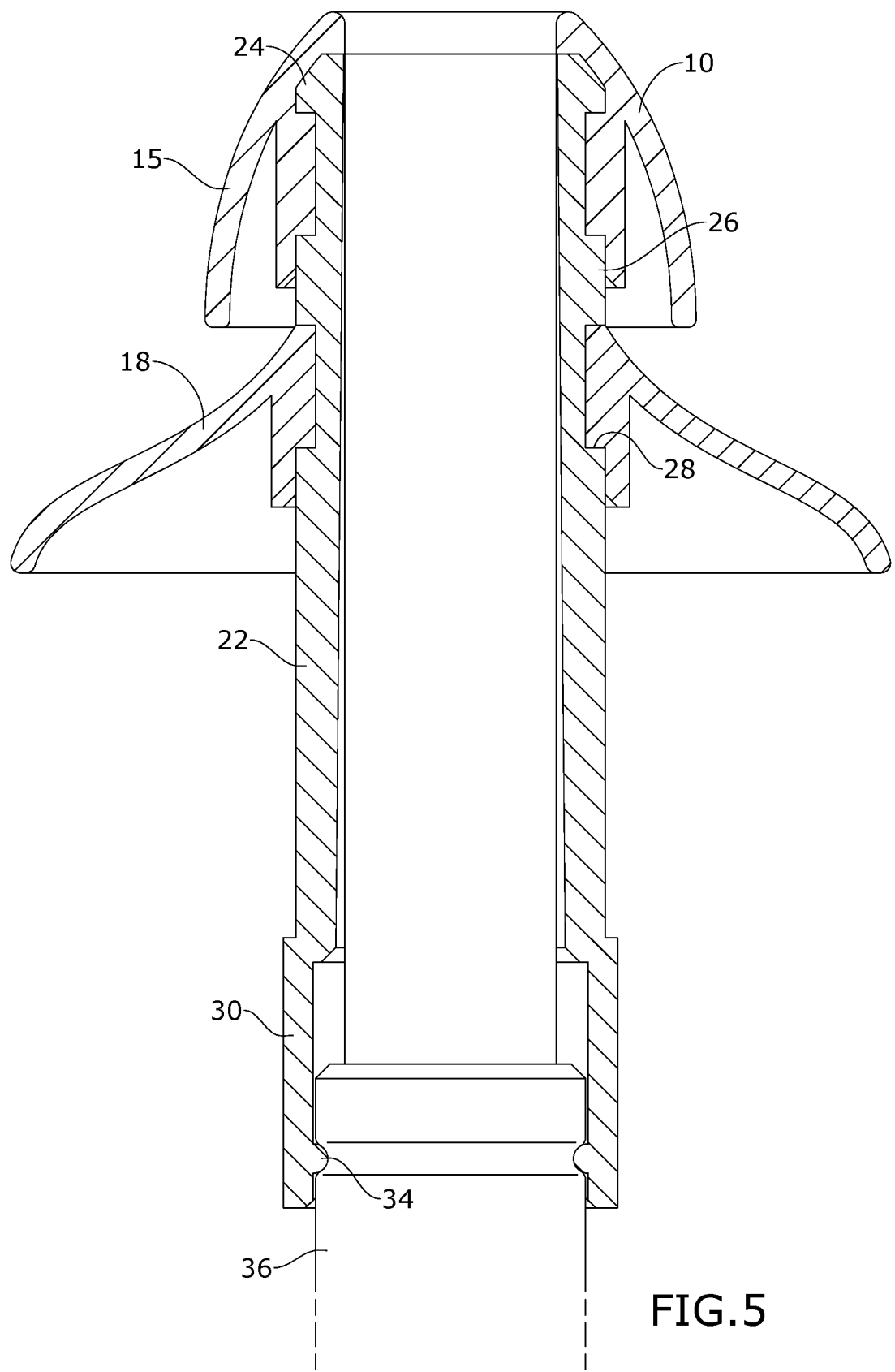
FIG. 5 depicts a cross-sectional view of certain embodiments of the protective cover apparatus taken along line 5-5 in FIG. 1.

In one embodiment as depicted in FIGS. 4-6, cap central tubular member 13 comprises an inner surface with upper groove 14 and lower groove 16. Upper groove 14 of cap central tubular member 13 is configured to engage with upper flange 24 of adapter 22 when cap 10 and adapter 22 are connected together. Similarly, lower groove 16 of cap central tubular member 13 is configured to engage with lower flange 26 of adapter 22 when cap 10 and adapter 22 are connected together. These connections ensure a secure fit between cap 10 and adapter 22.

In one embodiment as depicted in FIGS. 1-2 and 5, cap 10 and sleeve 18 are in contact with each other when the protective cover apparatus is assembled. However, it shall be appreciated that cap 10 and sleeve 18 can be separated from one another as desired by modifying the locations of upper flange 24, lower flange 26 and ridge 28 on adapter 22 in alternative embodiments.

In operation, the protective cover apparatus is coupled to the otoscope. In one embodiment as depicted in FIGS. 1-3 and 5-6, adapter 22 is coupled to camera head 36 of the otoscope by engaging protrusion 34 of tubular member 30 with attachment groove 38 of camera head 36. Sleeve 18 is disposed around tubular member 30 of adapter 22 and secured in place by engaging internal slot 20 of sleeve 18 with ridge 28 of adapter 22. Cap 10 is disposed around top end 23 of adapter 22 by engaging upper and lower grooves 14, 16 of cap 10 with corresponding upper and lower flanges 24, 26 of adapter 22.

As depicted in FIG. 7, the protective cover apparatus is inserted within the ear of the user and the otoscope is operated in the conventional manner. Specifically, the otoscope is maneuvered so that cap 10 and sleeve 18 insert into the ear canal of user 44. The opening formed by tubular member 30 of adapter 22, central tubular member 19 of sleeve 18, and cap central tubular member 13 and central opening 11 of cap 10 provides camera head 36 and the camera (not shown) of the otoscope unobstructed access to the ear canal of user 44. In one embodiment, a transparent cover layer is coupled to top end 23 of tubular member 30 to enhance cleanliness of the protective cover apparatus and otoscope. Flared surface 21 of sleeve 18 prevents the protective cover apparatus from entering into the ear canal of user 44 to a degree that can cause discomfort and/or damage to the ear canal or other internal members of the ear.

It shall be appreciated that the protective cover apparatus can be used in a wide variety of applications including, but not limited to, the examination of the nose, throat or other regions on the user. It shall be appreciated that the components of the protective cover apparatus described in several embodiments herein may comprise any alternative known materials in the field and be of any color, size and/or dimensions. It shall be appreciated that the components of the protective cover apparatus described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention, the scope of the invention is reflected by the breadth of the claims below rather than narrowed by the embodiments described above.

What is claimed is:

1. A protective cover apparatus for an otoscope to serve as a barrier between the otoscope and an ear canal of a user, the otoscope comprising a camera body coupled to a camera head having an attachment groove, the protective cover apparatus comprising:
   an adapter configured to attach to the camera head of the otoscope and comprising a tubular member with a top end, a bottom end opposite the top end, an inner surface and an outer surface;
   a sleeve coupled to the tubular member of the adapter and comprising a central tubular member having a top end and a bottom end, the sleeve comprising an outer flared surface protruding from the top end of the central tubular member; and
   a cap coupled to the top end of the tubular member of the adapter and comprising a central opening that permits unobstructed access to the camera head of the otoscope;
   wherein the otoscope is configured to be maneuvered to permit the cap and sleeve of the protective cover apparatus to enter the ear canal of the user, thereby allowing the protective cover apparatus to serve as a barrier between the otoscope and ear canal of the user.

2. The protective cover apparatus of claim 1, wherein the tubular member of the adapter comprises an upper flange on the outer surface, a lower flange on the outer surface, a ridge on the outer surface, and a protrusion on the inner surface proximate the bottom end of the tubular member of the adapter.

3. The protective cover apparatus of claim 2, wherein the protrusion of the tubular member of the adapter is configured to engage with the attachment groove of the camera head of the otoscope.

4. The protective cover apparatus of claim 3, wherein the central tubular member of the sleeve comprises an internal slot that is configured to engage with the ridge of the adapter.

5. The protective cover apparatus of claim 4, wherein the cap comprises a central tubular member comprising an inner surface with an upper groove and a lower groove, the upper groove of the cap configured to engage with the upper flange of the adapter and the lower groove of the cap configured to engage with the lower flange of the adapter.

6. The protective cover apparatus of claim 5, wherein the central tubular member of the cap comprises an outer surface that protrudes from a top end of the central tubular member of the cap.

7. The protective cover apparatus of claim 6, wherein the upper flange, lower flange and ridge are positioned on the tubular member of the adapter so that the cap and sleeve are in contact with each other.

8. The protective cover apparatus of claim 6, wherein the tubular member of the adapter is configured to allow the camera head of the otoscope to extend therethrough.

9. The protective cover apparatus of claim 8, further comprising a transparent cover layer coupled to the top end of the tubular member of the adapter.

10. The protective cover apparatus of claim 9, wherein the cap and sleeve are made from silicone.

\* \* \* \* \*